United States Patent

Yoshida (10) Patent No.: US 9,538,913 B2
(45) Date of Patent: Jan. 10, 2017

(54) OPHTHALMIC SYSTEM

(75) Inventor: Hirofumi Yoshida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/432,173

(22) Filed: Mar. 28, 2012

(65) Prior Publication Data

US 2012/0249963 A1    Oct. 4, 2012

(30) Foreign Application Priority Data

Mar. 31, 2011    (JP) .................. 2011-079364

(51) Int. Cl.
*A61B 3/10*    (2006.01)
*A61B 3/12*    (2006.01)
*A61B 3/14*    (2006.01)

(52) U.S. Cl.
CPC ............ *A61B 3/102* (2013.01); *A61B 3/12* (2013.01); *A61B 3/14* (2013.01)

(58) Field of Classification Search
CPC ............. A61B 3/10; A61B 3/102; A61B 3/12; A61B 3/13; A61B 3/14; A61B 3/145; A61B 3/15
USPC .................. 351/205–209; 17/208
See application file for complete search history.

(56) References Cited

U.S. PATENT DOCUMENTS

| | | | |
|---|---|---|---|
| 2003/0071911 A1* | 4/2003 | Shinohara et al. | 348/370 |
| 2007/0188706 A1* | 8/2007 | Pearson et al. | 351/206 |
| 2007/0222945 A1* | 9/2007 | Tsukada et al. | 351/205 |
| 2009/0149742 A1* | 6/2009 | Kato et al. | 600/425 |
| 2010/0238403 A1* | 9/2010 | Kobayashi et al. | 351/206 |
| 2010/0302508 A1* | 12/2010 | Yamamoto | A61B 3/102 351/206 |
| 2011/0176111 A1* | 7/2011 | Taki et al. | 351/207 |
| 2014/0028975 A1* | 1/2014 | Takai | 351/206 |

FOREIGN PATENT DOCUMENTS

| | | |
|---|---|---|
| CN | 101332077 A | 12/2008 |
| EP | 2347701 A1 | 7/2011 |
| JP | 2009-160190 A | 7/2009 |
| JP | 2009-160190 A | 7/2009 |
| JP | 2010-233998 A | 10/2010 |

OTHER PUBLICATIONS

Cirrus™ HD-OCT User Manual, May 2009, Carl Zeiss Meditec, Inc. pp. 1-1 to 2-28 and 3-1 to 3-22.*
RTVue, Model RT100 Users Manual Version 3.0, Release date Dec. 15, 2007, Optovue Inc. Fremont, CA 94538, pp. 5-1 to 5-16.*

* cited by examiner

*Primary Examiner* — Thomas K Pham
*Assistant Examiner* — Marin Pichler
(74) *Attorney, Agent, or Firm* — Canon U.S.A., Inc. IP Division (57) ABSTRACT

An ophthalmic system including an ophthalmic apparatus for acquiring an image of an anterior portion of a subject's eye and a tomographic image of the subject's eye includes a display control unit configured to cause a display unit to display the image of the anterior eye portion and the tomographic image, and an instruction unit configured to, if a pointer which indicates a point on the display unit is on the image of the anterior eye portion, give an instruction to change a distance between the subject's eye and the ophthalmic apparatus, and if the pointer is on the tomographic image, give an instruction to change the position of a coherence gate.

7 Claims, 4 Drawing Sheets

OPHTHALMIC SYSTEM

BACKGROUND OF THE INVENTION

Field of the Invention

The present invention relates to an ophthalmic system used in ophthalmologic examination and treatment.

Description of the Related Art

In recent years, apparatuses using optical coherence tomography (OCT) (hereinafter also referred to as "OCT apparatuses") have been put into practical use. OCT uses interference of low-coherence light to capture tomographic images. An OCT apparatus can capture a tomographic image of an object to be examined at a resolution corresponding to the wavelength of light that is incident on that object, thus enabling the obtained tomographic image to have a high resolution. The OCT apparatuses are particularly useful as ophthalmic apparatuses for acquiring tomographic images of a retina in an eye fundus.

Japanese Patent Application Laid-Open No. 2009-160190 discusses a technique in which, by operating a mouse, an examiner positions a cursor on a display screen for displaying an OCT tomographic image and then adjusts the position of a coherence gate.

Generally, before capturing a tomographic image with an OCT apparatus, alignment of an anterior eye portion, a focus position on a fundus, and a coherence gate position, for example, need to be adjusted. If these adjustments take time to perform, then a longer time will be required before an OCT image can be actually captured. This causes undesirable burden to the subject. The operability of the mouse or other input device is thus preferably increased to allow the examiner to make such adjustments efficiently.

SUMMARY OF THE INVENTION

According to an aspect of the present invention, an ophthalmic system includes an ophthalmic apparatus for acquiring an image of an anterior eye portion of a subject's eye and at least one other image formed of at least one of a tomographic image of the subject's eye and an image of a fundus of the subject's eye. The system includes a display control unit configured to cause a display unit to display the image of the anterior eye portion, the at least one other image, and a pointer for indicating either the image of the anterior eye portion or the at least one other image, a control unit configured to adjust a working distance between the ophthalmic apparatus and the subject's eye in a case that a user causes the pointer to indicate the image of the anterior eye portion and the user issues an instruction, adjust the focus of the image of the fundus of the subject's eye in a case that the at least one other image includes the image of the fundus of the subject's eye, the user causes the pointer to indicate the image of the fundus of the subject's eye, and the user issues an instruction, and adjust the position of a coherence gate in a case that the at least one other image includes the tomographic image of the subject's eye, the user causes the pointer to indicate the tomographic image of the subject's eye, and the user issues an instruction.

According to an aspect of the present invention, if a display unit includes thereon display areas for respectively displaying a plurality of images, an examiner can give an instruction to make an adjustment (a change) corresponding to the image on one of the display areas on which the examiner has positioned a pointer (for example, a cursor), which is configured to indicate a portion on the display unit. Hence, the examiner can easily make adjustments by moving the pointer on the display screen. This configuration can increase the operability of the mouse and shorten the length of time before images can be actually captured, and thus the burden to the subject can be reduced.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 3 (including FIGS. 3A and 3B) is a flow chart illustrating processing performed by the respective components in the ophthalmic system according to the exemplary embodiment.

DESCRIPTION OF THE EMBODIMENTS

Various exemplary embodiments, features, and aspects of the invention will be described in detail below with reference to the drawings.

An ophthalmic system (or an ophthalmic apparatus) according to an exemplary embodiment of the present invention includes a display unit including thereon display areas for respectively displaying a plurality of images. Thus, an examiner can give an instruction to make an adjustment (a change) corresponding to the image on one of the display areas on which the examiner has positioned a pointer (for example, a cursor), which is configured to indicate a portion on the display unit. Hence, the examiner can easily make adjustments by moving the pointer on the display screen. This configuration can increase the operability of the mouse and shorten the length of time before images can be actually captured, and thus the burden to the subject can be reduced.

The term "coherence gate" as used herein means a position in an optical path of a measuring beam corresponding to an optical path of a reference beam. The position of the coherence gate can be changed by varying a difference in optical path length between the measuring beam and the reference beam using an optical-path-length difference changing unit. The optical-path-length difference changing unit may be configured to move the position of a reference mirror along the optical axis, or may be configured to move the apparatus along the optical axis with respect to the subject's eye. Examples of the optical-path-length difference changing unit may include a movable stage provided for the reference mirror and the apparatus.

<General Configuration of Apparatus>

Figure 2A:
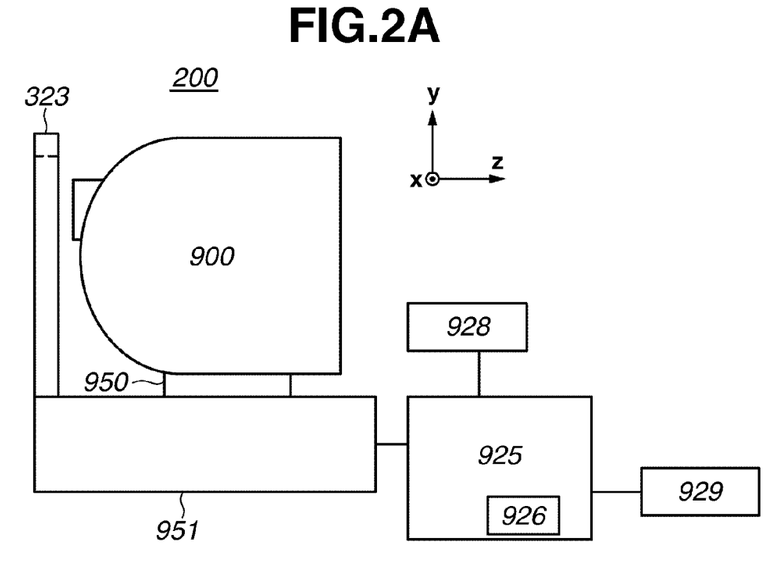
FIGS. 2A and 2B illustrate components in an ophthalmic apparatus according to the exemplary embodiment.

The general configuration of an ophthalmic apparatus according to the exemplary embodiment will be described with reference to FIG. 2A, which is a side view thereof. An optical head 900 is a measuring optical system for obtaining an image of an anterior eye portion, and a two-dimensional image and a tomographic image of a fundus of the eye. With a stage unit 950 (also referred to as a moving unit), the optical head 900 is movable with respect to a base unit 951. The stage unit 950 is moved by a motor or the like in X-, Y-, and Z-directions in FIG. 2A. The base unit 951 includes a spectroscope which will be described below.

A personal computer 925, which serves as a control unit for the stage unit 950 as well, can constructs tomographic images, while controlling the stage unit 950. A hard disk 926, which also serves as a storage unit for storing information about a subject, stores a program for capturing tomographic images, for example. A display control unit (not illustrated) causes a display unit 928, such as a monitor, to display acquired images and other images. An input unit (an instruction unit) 929 provides an instruction to the personal computer 925. More specifically, the input unit 929 includes a keyboard and a mouse (also referred to as a pointing device). A chinrest 323 is provided to fix a chin and a forehead of a subject.

(Configurations of Measuring Optical System and Spectroscope)

Figure 2B:
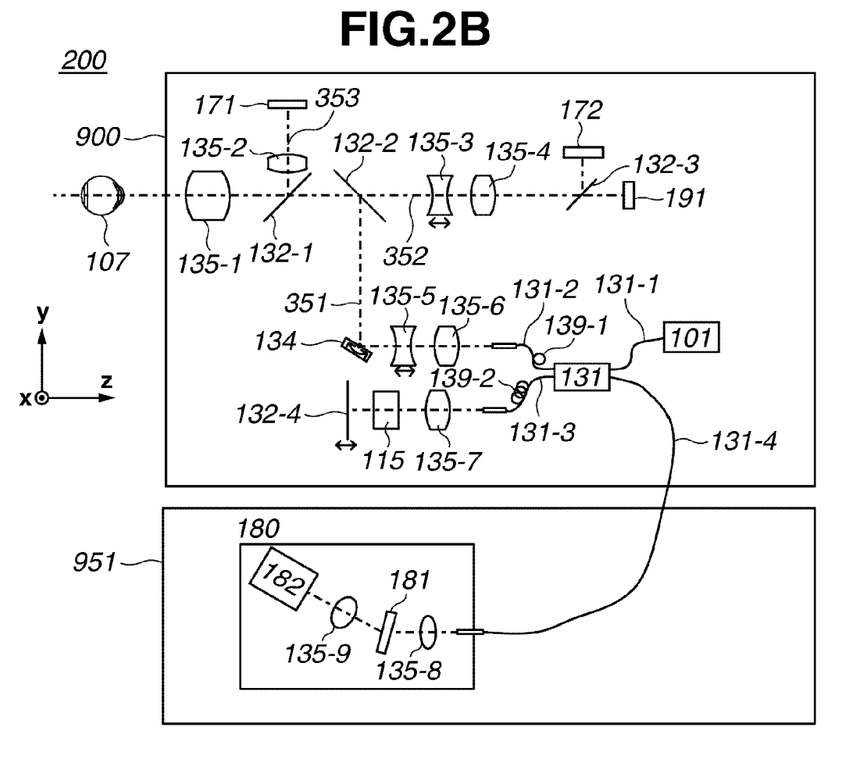

The configurations of the measuring optical system and a spectroscope in the ophthalmic apparatus according to the present exemplary embodiment will be described below with reference to FIG. 2B.

The internal configuration of the optical head 900 will be first described. An objective lens 135-1 is placed to face a subject's eye 107. On an optical axis of the objective lens 135-1, a first dichroic mirror 132-1 and a second dichroic mirror 132-2 split light by wavelength band into an optical path 351 of an OCT optical system, an optical path 352 for observation of the fundus and for a fixation lamp, and an optical path 353 for observation of the anterior eye portion. Likewise, a third dichroic mirror 132-3 splits the light in the optical path 352 by wavelength band into an optical path to a fundus observation charge-coupled device (CCD) 172 and an optical path to a fixation lamp 191. The optical head 900 further includes lenses 135-3 and 135-4. The lens 135-3 is driven by a motor (not illustrated) to adjust focusing for the fixation lamp and for observation of the fundus.

The CCD 172 has sensitivity to the wavelength of illumination light (not illustrated) provided for observation of the fundus, specifically, a wavelength of about 780 nm. The fixation lamp 191 produces visible light to facilitate fixation of the subject's eye 107. The optical system for observation of the fundus may include an optical system, such as a scanning laser ophthalmoscope (SLO), for example. In the optical path 353, a lens 135-2 and an anterior eye observation infrared CCD 171 are provided. The CCD 171 has sensitivity to the wavelength of illumination light (not illustrated) provided for observation of the anterior eye portion, specifically, a wavelength of about 970 nm. Further, in the optical path 353, an image splitting prism (not illustrated) is provided, enabling the distance from the optical head 900 to the subject's eye 107 in the Z-direction to be detected as split images obtained in an anterior eye observation image.

The optical path 351 forms the OCT optical system as described previously and is used to acquire tomographic images of the fundus of the subject's eye 107. More specifically, the optical path 351 is used to obtain an interference signal for forming a tomographic image. An XY scanner 134 scans the fundus with a light beam. The XY scanner 134, illustrated as a mirror, performs scanning in the two axial directions X and Y. The optical head 900 further includes lenses 135-5 and 135-6. The lens 135-5 is driven by a motor (not illustrated) to perform a focus adjustment for focusing a light beam from a light source 101 emitted from a fiber 131-2 onto the fundus of the subject's eye 107. The fiber 131-2 is connected to an optical coupler 131. Concurrently, due to the focus adjustment, light from the fundus of the subject's eye 107 forms a spot image and is incident on an edge of the fiber 131-2.

The configurations of the optical path from the light source 101, a reference optical system, and a spectroscope will be described below. The light source 101, a mirror 132-4, a dispersion compensation glass 115, the optical coupler 131, single-mode optical fibers 131-1 to 131-4, which are connected to the optical coupler 131 as an integral part thereof, a lens 135-7, and a spectroscope 180 form a Michelson interferometer.

A light beam emitted from the light source 101 travels through the optical fiber 131-1 and the optical coupler 131 in which the light beam is split into a measuring beam to the optical fiber 131-2 and a reference beam to the optical fiber 131-3. The measuring beam travels through the optical path of the above-described OCT optical system to illuminate the fundus of the subject's eye 107, which is an object to be observed. The measuring beam is reflected and scattered by the retina, and thus travels to the optical coupler 131 through the same optical path. The reference beam passes through the optical fiber 131-3, the lens 135-7, and the dispersion compensation glass 115 to reach the mirror 132-4 for reflection. The dispersion compensation glass 115 is inserted to compensate for dispersion of the measuring beam and the reference beam. The reference beam returns through the same optical path to the optical coupler 131. The optical coupler 131 combines the measuring beam and the reference beam into interference light (also referred to as combined light). When the measuring beam and the reference beam have substantially the same optical path length, interference occurs. The mirror 132-4 is held by a motor and a drive mechanism (not illustrated) so as to be adjustable in the direction of the optical axis. Thus, the optical path length of the reference beam can be adjusted to be equal to the optical path length of the measuring beam that varies depending on the subject's eye 107. The interference light is guided to the spectroscope 180 via the optical fiber 131-4.

A polarization adjusting unit 139-1 for the measuring beam is provided in the optical fiber 131-2. A polarization adjusting unit 139-2 for the reference beam is provided in the optical fiber 131-3. The polarization adjusting units 139-1 and 139-2 include some portions of the optical fibers 131-2 and 131-3 each routed in the shape of a loop. The polarization states of the measuring beam and the reference beam can be adjusted to each other by turning these loop-shaped portions with the longitudinal direction of each fiber being the center, and thereby twisting the fibers 131-2 and 131-3. In the apparatus according to the present exemplary embodiment, the polarization states of the measuring beam and the reference beam are adjusted and fixed in advance. The spectroscope 180 includes lenses 135-8 and 135-9, a diffraction grating 181, and a line sensor 182. The interference light emitted from the optical fiber 131-4 is collimated into approximately parallel light by the lens 135-8. The parallel light is then dispersed by the diffraction grating 181 to form an image on the line sensor 182 through the lens 135-3.

The light source 101 and its periphery will be described in more detail below. The light source 101 is a super luminescent diode (SLD), a typical low-coherence light source. The light source 101 has a center wavelength of 855 nm and a wavelength bandwidth of about 100 nm. The bandwidth, which affects the resolution of an acquired tomographic image in the direction of the optical axis, is an important parameter. In the present exemplary embodiment, the type of light source employed is an SLD. However, any other type of light source, for example, an amplified spontaneous emission (ASE) device, may also be used so long as low-coherence light can be emitted. Since a human eye is an object to be measured, near infrared light is suitable as the center wavelength. The center wavelength, which affects the resolution of an acquired tomographic image in the transverse direction, is preferably a short wavelength. For those two reasons, the center wavelength is set to 855 nm.

In the present exemplary embodiment, a Michelson interferometer is employed. However, a Mach-Zehnder interferometer may also be used. When a difference in the amount of light between the measuring beam and the reference beam is relatively small, a Michelson interferometer, in which a single splitting and combining unit is provided, is preferable to a Mach-Zehnder interferometer, in which a splitting unit and a combining unit are provided separately.

<Method for Acquiring Tomographic Image>

Next, a method for acquiring a tomographic image will be described. A control unit (not illustrated) acquires a tomographic image of a desired portion of the fundus of the subject's eye 107 by controlling the XY scanner 134. First, the measuring beam 105 is scanned in the X-direction, so that information for a predetermined number of imaging lines is captured by the line sensor 182 from an imaging area on the fundus in the X-direction. A fast Fourier transform (FFT) is performed on a luminance distribution on the line sensor 182 obtained at a position in the X-direction. The linear luminance distribution resulting from the FFT is converted into density information or color information for display on the monitor 928. This density or color information is referred to as an A-scan image. A two-dimensional image obtained by arranging a plurality of A-scan images is referred to as a B-scan image. After capturing a plurality of A-scan images for constructing a single B-scan image, the scanning position in the Y-direction is moved, and scanning is performed again in the X-direction to obtain a plurality of B-scan images. The examiner can make a diagnosis on the subject's eye 107 by looking at the plurality of B-scan images or a three-dimensional tomographic image constructed from the plurality of B-scan images, displayed on the monitor 928.

<Flow of Capturing Tomographic Image>

Figures 3, 3A:
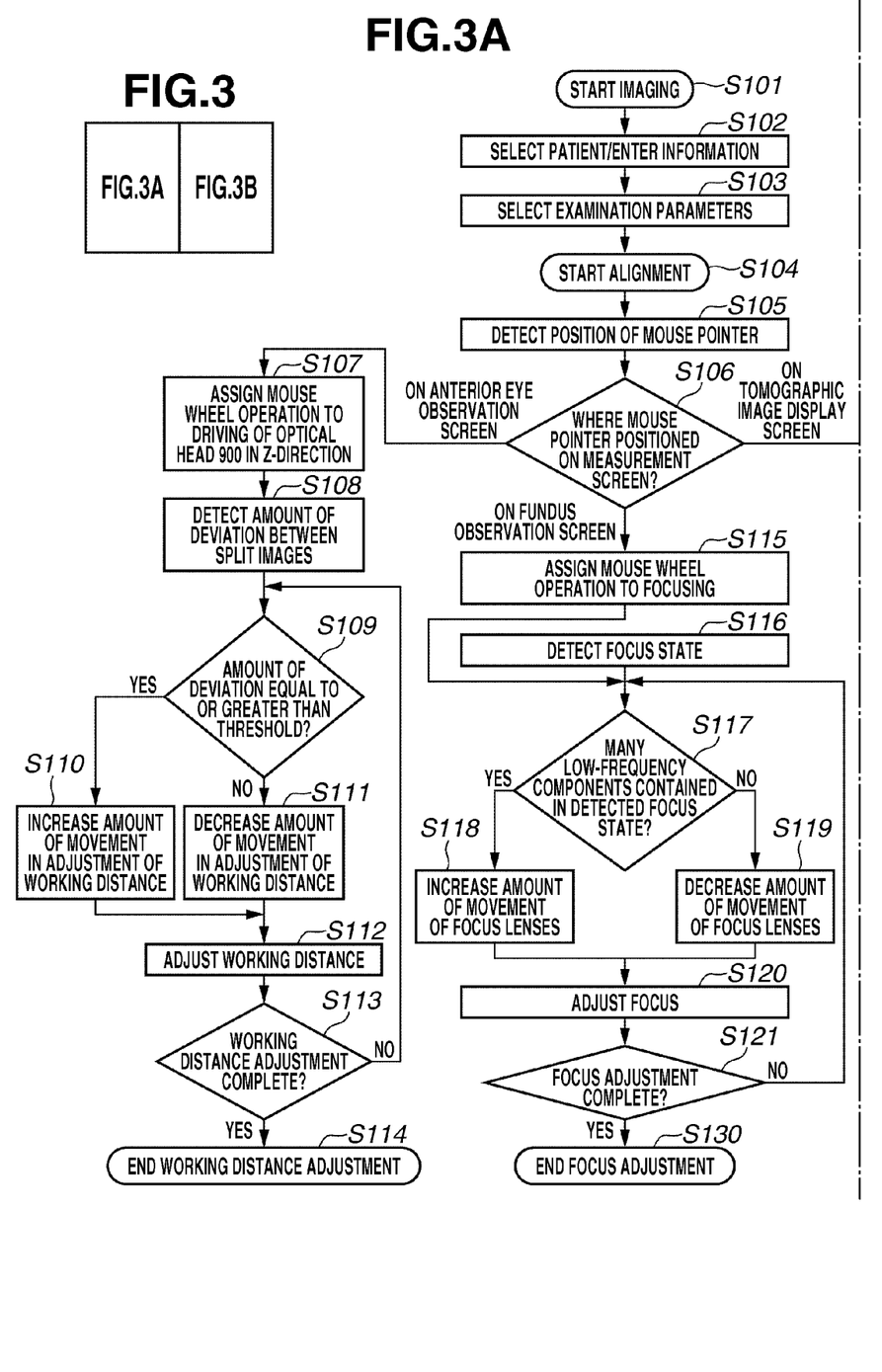

Referring to a flow chart in FIG. 3 (including FIGS. 3A and 3B), adjustments made to acquire a tomographic image will be described. First, in step S101, an imaging process (a process for acquiring a tomographic image) is started. The personal computer 925 executes a program for imaging to start a screen for imaging on the monitor 928. At the same time, the personal computer 925 effects the operation of the XY scanner 134. Then, the process automatically proceeds to step S102.

Figure 3B:
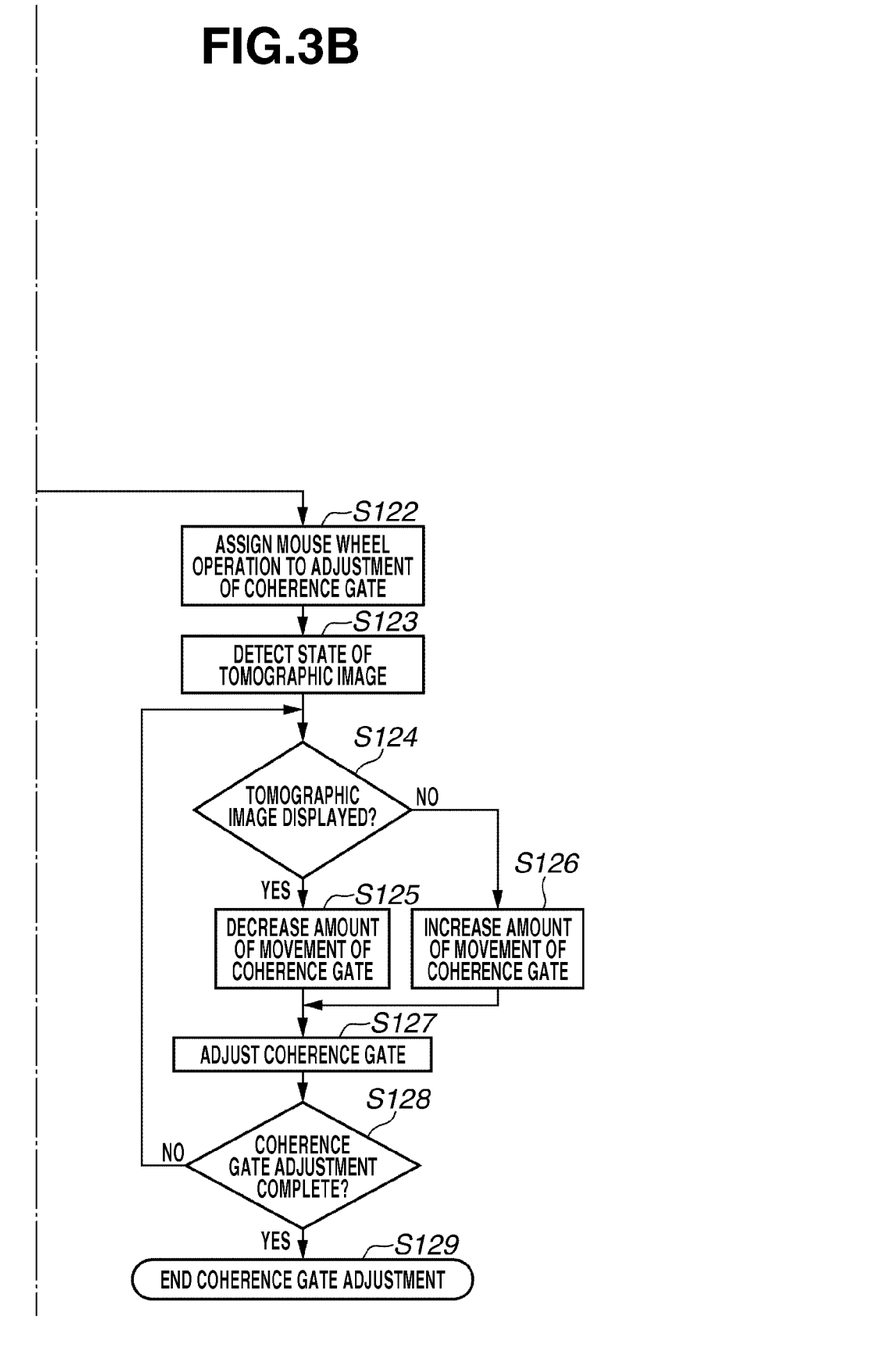

Next, in step S102, the examiner causes the monitor 928 to display a patient information input screen, and selects the patient or, in the case of a first visit of a new patient, enters patient information. When the examiner operates the mouse or other input device (for example, clicks on an OK button displayed on the patient information input screen with the mouse), the process proceeds to step S103.

In step S103, the examiner causes the monitor 928 to display an examination parameter selection screen. The examiner sets, as examination parameters, the right or left eye as the subject's eye to be examined, an area in which a tomographic images is to be captured, the number of tomographic images to be captured, and the number of A-scan images to be contained in each B-scan image, for example. Settings made to capture tomographic images are referred to as a scan pattern. When the examiner performs an operation (for example, clicks on an OK button displayed on the examination parameter selection screen with the mouse), the process proceeds to step S104.

<Measurement Screen>

Figure 1A:
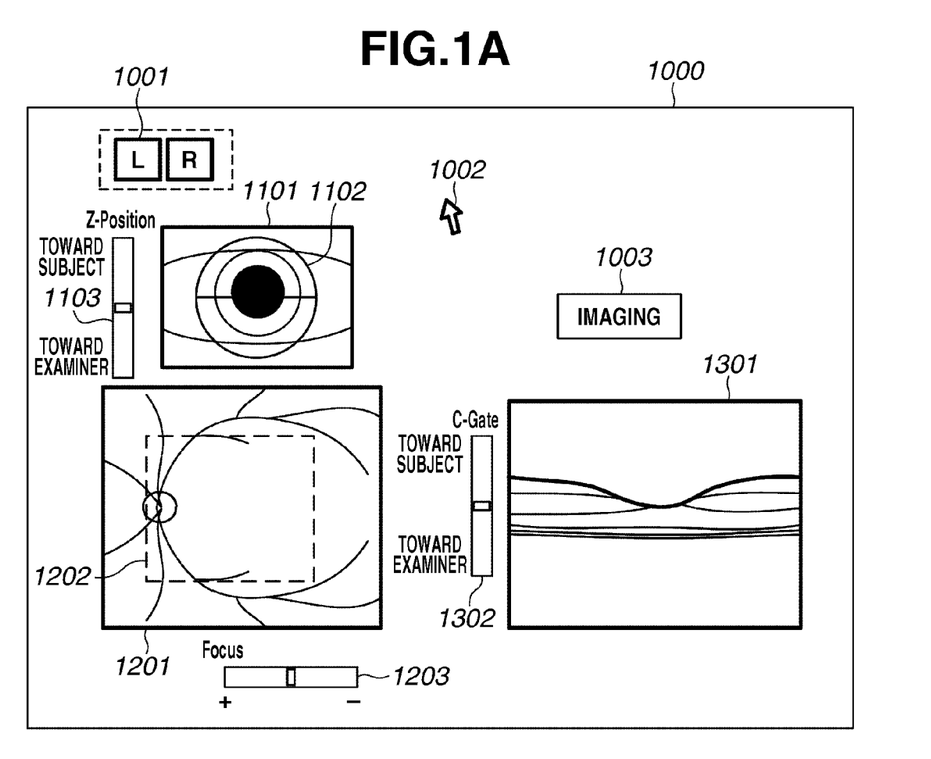
FIG. 1A illustrates a measurement screen of an ophthalmic system according to an exemplary embodiment.
Figure 1B:
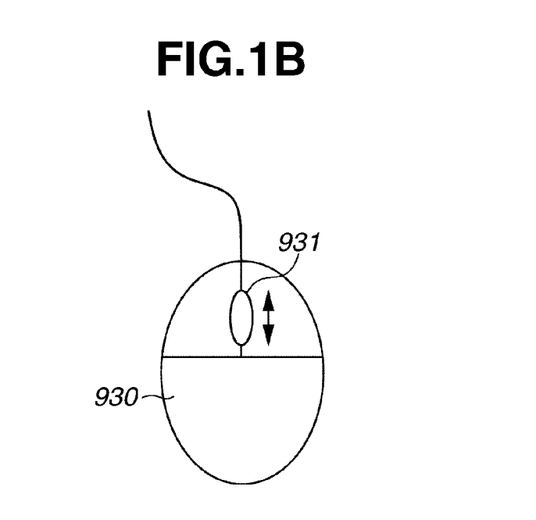
FIG. 1B illustrates a mouse with a mouse wheel.

With reference to FIGS. 1A and 1B, a measurement screen 1000, which is displayed in the display screen in step S104, will be described. An anterior eye observation screen 1101 displays an image acquired by the anterior eye observation CCD 171. A fundus two-dimensional image display screen 1201 (also referred to as a fundus observation screen) displays an image acquired by the fundus observation CCD 172. A tomographic image display screen 1301 is used to examine an acquired tomographic image. Buttons 1001 are used to switch the subject's eye between the right and left eyes. When the examiner presses either the L or R button, the optical head 900 is moved to the position of the left or right eye corresponding to the pressed button. As the examiner moves the mouse on a desk, for example, a position of the cursor 1002 moves correspondingly.

In the ophthalmic apparatus according to the present exemplary embodiment, alignment or the like may be changed according to the position of the cursor 1002 detected by a position detecting unit (not illustrated). The position detecting unit (not illustrated) can calculate the position of the cursor 1002 from the pixel position of the cursor 1002 on the display screen. Predetermined areas are defined on the display screen. When the cursor 1002 is positioned within the pixels of those predetermined areas, the examiner can perform respective adjustments determined for those areas. The examiner can operate the mouse by rotating a mouse wheel. As illustrated in FIG. 1B, generally a mouse wheel 931 is disposed on an upper portion of the mouse 930. By rotating the mouse wheel 931, the examiner can give instructions to make adjustments, for example, an alignment adjustment. The examiner can also give instructions to make adjustments, such as an alignment adjustment, by operating the mouse 930 differently, for example, by dragging. After completion of adjustments, such as an alignment adjustment, the examiner presses an imaging button 1003 to capture a required image.

Sliders which are disposed in the vicinity of the respective images are used to make adjustments. A slider 1103 is used to adjust the position of the optical head 900 in the Z-direction with respect to the subject's eye 107. A slider 1203 is used to adjust the focus position. A slider 1302 is used to adjust the coherence gate position. In adjusting the focus position, the lenses 135-3 and 135-5 are moved in the directions indicated by arrows illustrated in FIG. 2B to make an adjustment for achieving focus on the fundus. In adjusting the coherence gate position, the mirror 132-4 is moved in the directions indicated by an arrow illustrated in FIG. 2B to allow observation of the tomographic image in a desired position on the tomographic image display screen 1301. Mouse operations performed with the cursor 1002 being positioned on these images also cause corresponding movements of the respective sliders 1103, 1203, and 1302.

In step S105, the position of the cursor 1002 is detected. More specifically, the position of the cursor 1002 on the screen is detected. In step S106, the next step to which the process proceeds depends on where the cursor 1002 is positioned in the plurality of areas. If the cursor 1002 is positioned on the anterior eye observation screen 1101, the process proceeds to step S107, if on the fundus observation screen 1201, then to step S115, and if on the tomographic image display screen 1301, then to step S122. Specific relationships between the area in which the cursor 1002 is positioned and corresponding adjustment will be described.

<Adjustment of Alignment of Anterior Portion of Eye>

If, in step S106, it is determined that the cursor 1002 is on the anterior eye observation screen (also referred to as a first area) 1101, then in step S107, the mouse wheel operation is assigned to driving the optical head 900 in the X-, Y-, and Z-directions. Split images 1102 are displayed on the anterior eye observation screen 1101, so that the distance (i.e., a working distance) in the Z-direction between the subject's eye 107 and the objective lens 135-1 in the optical head 900 can be detected. For example, in the case of automatic alignment, after the upper and lower split images 1102 of the anterior eye portion are aligned, (that is, after completion of alignment in the X- and Y-directions), the position of the optical system is automatically adjusted to achieve a desired working distance. If a manual operation is selected, and then the cursor 1002 is positioned on the anterior eye observation screen 1101, the working distance (the distance in the Z-direction from the objective lens 135-1 in the optical head 900 to the subject's eye 107) is adjusted by a mouse operation.

In step S108, a deviation amount between the split images 1102 is detected. By detecting the deviation amount between the split images 1102, a deviation amount of the working distance from the desired distance can be calculated. If the deviation amount is large, a movement amount (also referred to as a change amount) of the optical head 900 with respect to the subject's eye 107 is preferably increased (which means coarse alignment). Whereas if the deviation amount is small, the movement amount of the optical head 900 with respect to the subject's eye 107 is preferably decreased (which means fine alignment). To achieve such an operation, the movement amount of the optical system with respect to an instruction amount (e.g., an amount of mouse scrolling, or the number of steps per unit time caused by scrolling) indicated by an instruction unit, such as the mouse, is varied. Examples of the movement amount of the optical system (also referred to as the sensitivity of mouse operation) include the change amount with respect to the above-described number of steps per unit time. The center position of the pupil is calculated by detecting the edge of the pupil in each of the upper and lower split images 1102. By comparing the calculated pupil center positions in the upper and lower split images 1102, the deviation amount can be obtained.

In step S109, it is determined whether the deviation amount between the split images 1102 is equal to or greater than a threshold. The deviation amount detected as described above is compared with a predetermined threshold (a predetermined value).

If the deviation amount is equal to or greater than the threshold (the predetermined value) (YES in step S109), then in step S110, the movement amount described above (the sensitivity of mouse operation) is increased to perform coarse alignment.

Whereas if the deviation amount is smaller than the threshold (the predetermined value) (NO in step S109), then in step S111, the movement amount (the sensitivity of mouse operation) is decreased to perform fine alignment. The threshold may be set in advance or may be set in such a manner that the examiner can change the value thereof. The sensitivity of mouse operation may also be changed according to the deviation amount between the split images 1102 without setting the threshold.

In step S112, the working distance is adjusted based on the movement amount set as described above.

In step S113, it is determined whether the adjustment of the working distance is completed. If the examiner or the personal computer 925 determines that the upper and lower split images 1102 are properly aligned (YES in step S113), then the process proceeds to step S114 where the adjustment of the working distance is ended. If the examiner or the personal computer 925 determines that the upper and lower split images 1102 are not properly aligned (NO in step S113), then the process returns to step S109. In this manner, alignment is performed on the anterior eye observation screen 1101.

<Adjustment of Focus Position on Fundus>

If, in step S106, it is determined that the cursor 1002 is on the fundus observation screen (also referred to as a second or third area) 1201, then in step S115, the mouse wheel operation is assigned to driving the focus lenses 135-3 and 135-5. On the fundus observation screen 1201, a tomographic image capture area 1202 set in advance is displayed so as to be checked by the examiner. When the examiner positions the cursor 1002 on this image, the mouse operation is assigned to driving the focus lenses 135-3 and 135-5 to perform focus adjustments.

In step S116, a focus state is detected. The focus state is detected by analyzing frequency components of the image on the fundus observation screen 1201.

In step S117, it is determined whether many low-frequency components are contained in the detected focus state. If the image on the fundus observation screen 1201 contains many low-frequency components (YES in step S117), the focus lenses 135-3 and 135-5 need to be moved significantly because focusing is far from an in-focus state. Whereas if the image on the fundus observation screen 1201 contains many high-frequency components (NO in step S117), fine focus adjustment is required because focusing is close to the in-focus state. Taking this difference into account, the movement amount of the focus position with respect to the mouse operation is changed. The amounts of the two types of frequency components (low-frequency components and high-frequency components) determined in advance according the fundus structure are calculated and compared, so that the focus state is detected.

Accordingly, in step S117, it is determined whether many low-frequency components are contained in the detected focus state. The amounts of two types of frequency components detected as described above are compared with a predetermined threshold (a predetermined amount) for the low-frequency components and a predetermined threshold (a predetermined amount) for the high-frequency components.

If the amount of low-frequency components is greater than the threshold thereof, and the amount of high-frequency components is smaller than the threshold thereof, then it can be determined that the fundus image obtained at this focus position contains many low-frequency components (YES in step S117). In this case, in step S118, the movement amount (also referred to as the change amount) of the focus position is set to a large amount.

If the amount of low-frequency components is smaller than the threshold thereof, and the amount of high-frequency components is greater than the threshold thereof, it can be determined that the amount of low-frequency components contained in the fundus image obtained at this focus position is small (NO in step S117). In this case, in step S119, the movement amount of the focus position is set to a small amount. This allows fine adjustment of the focus position. These thresholds may be set in advance or may be set in such a manner that the examiner can change the values thereof. The sensitivity of mouse operation may be set to a unique value according to the two types of frequency components.

The sensitivity of mouse operation may also be changed based on a comparison in magnitude between the deviation amount occurring between split-target images of a split target (not illustrated) projected onto the fundus and threshold thereof.

In step S120, the focus is adjusted based on the movement amount set as described above.

In step S121, it is determined whether the focus adjustment is completed. If the examiner or the personal computer 925 determines that the focus has been adjusted within a desired range (YES in step S121), the process proceeds to step S130 to end the focus adjustment. If the examiner or the personal computer 925 determines that the focus has not been adjusted within the desired range (NO in step S121), the process returns to step S117. In this manner, focus adjustment is performed on the fundus observation screen 1201.

<Adjustment of Position of Coherence Gate>

If, in step S106, it is determined that the cursor 1002 is on the tomographic image display screen (also referred to as the second area) 1301, then in step S122, the mouse wheel operation is assigned to driving the coherence gate 132-4. When the cursor 1002 is positioned on the tomographic image display screen 1301, the position of the coherence gate is changed by operating the mouse. In step S123, the state of a tomographic image is detected.

In step S124, it is determined whether a tomographic image is displayed on the tomographic image display screen 1301. In adjusting the position of the coherence gate, the movement amount (also referred to as the change amount) of the position of the coherence gate with respect to the mouse operation is changed according to whether a tomographic image is displayed on the tomographic image display screen 1301 or not. More specifically, if a tomographic image is not displayed on the tomographic image display screen 1301, the movement amount described above is increased. If a tomographic image is displayed, the movement amount is decreased. More specifically, an output from the line sensor 182 is subjected to wave conversion, Fourier transform, and other required processing to obtain A-scan information of a tomographic image. The determination described above is made according to whether the A-scan information includes a luminance value equal to or higher than a noise level.

In step S124, if the A-scan information includes the luminance value equal to or higher than the noise level, it is determined that the tomographic image is displayed on the tomographic image display screen 1301 (YES in step S124). Then in step S125, the movement amount of the coherence gate is set to a small amount.

Whereas if the luminance value is less than the noise level, it is determined that the tomographic image is not displayed on the tomographic image display screen 1301 (NO in step S124). Then in step S126, the movement amount of the coherence gate is set to a large amount.

In step S127, the coherence gate is adjusted based on the movement amount of the coherence gate set as described above.

In step S128, it is determined whether the adjustment of the coherence gate is completed. If the examiner or the personal computer 925 determines that the coherence gate has been adjusted within a desired range (YES in step S128), then the process proceeds to step S129 to end the adjustment of the coherence gate. If the examiner or the personal computer 925 determines that the coherence gate has not been adjusted within the desired range (NO in step S128), then the process returns to step S124. In this manner, adjustments of the coherence gate are performed on the tomographic image display screen 1301.

As set forth above, with the ophthalmic apparatus according to the present exemplary embodiment, the examiner can make necessary adjustments while directly observing the image. Hence, the operation is simplified, and the adjustments can be performed efficiently. In the foregoing description, the alignment, focus, and coherence gate are adjusted manually, but may also be automatically adjusted in this order.

The ophthalmic apparatus may also be configured in such a manner that the examiner can select on the measurement screen 1000 either a manual mode in which these adjustments are made manually or an automatic mode in which these adjustments are made automatically. In that case, if the examiner selects the automatic mode, the manual mode (in which the examiner can give an instruction to make a change using the instruction unit) may be automatically selected after completion of the automatic adjustments. Such a configuration enables the examiner to manually make fine adjustments after automatic coarse adjustments, so that the efficiency of the adjustments can be increased.

Aspects of the present invention can also be realized by performing the following process. More specifically, software (a program) for realizing the functions of the above described exemplary embodiment is supplied to a system or an apparatus via a network or from a recording medium of various types. A computer (such as a central processing unit (CPU) and a microprocessor unit (MPU)) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-079364 filed Mar. 31, 2011, which is hereby incorporated by reference herein in its entirety.

What is claimed is:

1. An ophthalmic system comprising:
an ophthalmic apparatus for capturing an image of an anterior eye portion of a subject's eye, a tomographic image of a fundus of the subject's eye, and an image of the fundus of the subject's eye, the tomographic image being formed based on combined light obtained by combining return light from the subject's eye to be inspected irradiated with measuring light and reference light which is reflected by a reference mirror;
a display control unit configured to cause a display unit to simultaneously display the captured image of the anterior eye portion, the captured tomographic image, the captured image of the fundus, and a pointer for indicating an arbitrary position in the display unit;
a detection unit configured to detect a position of the pointer in the display unit; and
a control unit configured to receive an instruction from a mouse,
wherein in response to receiving an instruction indicating a rotation of a wheel of the mouse, the control unit adjusts a physical working distance between the ophthalmic apparatus and the subject's eye, in a case that the detection unit detects that the pointer is positioned within the captured image of the anterior eye portion;
wherein in response to receiving the instruction indicating the rotation of the wheel of the mouse, the control unit adjusts a physical position of a lens within the ophthalmic apparatus relative to other optical components of the ophthalmic apparatus, wherein the adjustment of the physical position of the lens is for focusing of the image of the fundus of the subject's eye, in a case that the detection unit detects that the pointer is positioned within the captured image of the fundus of the subject's eye;

wherein in response to receiving the instruction indicating the rotation of the wheel of the mouse, the control unit adjusts a physical position of the reference mirror within the ophthalmic apparatus relative to other optical components of the ophthalmic apparatus, wherein the adjustment of the physical position of the reference mirror is for adjusting a coherence gate, in a case that the detection unit detects that the pointer is positioned within the captured tomographic image of the subject's eye, and wherein the mouse is operable by the user to control a position of the pointer in the display unit.

2. An ophthalmic system according to claim 1, wherein the ophthalmic apparatus comprises an optical range finder for generating split images and a detection unit for detecting an amount of deviation between the split images, the ophthalmic apparatus being configured so that, in a case where the deviation between the split images is above a threshold, the working distance is varied more quickly in response to the instruction indicating the rotation of the wheel of the mouse while the pointer is positioned within the captured image of the anterior eye portion, than in case where the deviation between the split images is below the threshold.

3. An ophthalmic system according to claim 1, wherein the ophthalmic apparatus comprises a focus detection unit for detecting whether or not the image of the fundus of the subject's eye is in focus, the ophthalmic apparatus being configured so that, in a case where the focus detection unit detects that the image is further out of focus than a threshold, the focus of the image of the fundus is varied more quickly in response to the instruction indicating the rotation of the wheel of the mouse while the pointer is positioned within the captured image of the fundus of the subject's eye, than in a case where the detection unit detects that the focus is closer the threshold.

4. An ophthalmic system according to claim 1, wherein the ophthalmic apparatus comprises a detection unit for detecting a state of the tomographic image, the ophthalmic apparatus being configured so that, in a case where the detection unit detects that the tomographic image is not displayable, the coherence gate is varied more quickly in response to the instruction indicating the rotation of the wheel of the mouse while the pointer is positioned within the captured tomographic image of the subject's eye, than in in a case where the detection unit detects that the tomographic image is displayable.

5. The ophthalmic system according to claim 1, wherein the pointer is a cursor operable by the mouse.

6. A method for an ophthalmic system comprising an ophthalmic apparatus for capturing an image of an anterior eye portion of a subject's eye, a tomographic image of a fundus of the subject's eye, and an image of the fundus of the subject's eye, the tomographic image being formed based on combined light obtained by combining return light from the subject's eye to be inspected irradiated with measuring light and reference light which is reflected by a reference mirror, the method comprising:

simultaneously displaying the image of the anterior eye portion, the tomographic image, the image of the fundus, and a pointer for indicating an arbitrary position on a display unit;

detecting a position of the pointer on the display unit;

in response to receiving an instruction indicating a rotation of a wheel of the mouse, adjusting a physical working distance between the ophthalmic apparatus and the subject's eye, in a case that it is detected that the pointer is positioned within the captured image of the anterior eye portion;

in response to receiving the instruction indicating the rotation of the wheel of the mouse, adjusting a physical position of a lens within the ophthalmic apparatus relative to other optical components of the ophthalmic apparatus, wherein the adjustment of the physical position of the lens is for focusing of the image of a fundus of the subject's eye, in a case that it is detected that the pointer is positioned within the captured image of the fundus of the subject's eye; and in response to receiving the instruction indicating the rotation of the wheel of the mouse, adjusting a physical position of the reference mirror within the ophthalmic apparatus relative to other optical components of the ophthalmic apparatus, wherein the adjustment of the physical position of the reference mirror is for adjusting a coherence gate, in a case that it is detected that the pointer is positioned within the captured tomographic image of the subject's eye, and wherein the mouse is operable by the user to control a position of the pointer on the display unit.

7. A non-transitory computer-readable storage medium storing a program that causes a computer to execute a method for an ophthalmic system comprising an ophthalmic apparatus for capturing an image of an anterior eye portion of a subject's eye, a tomographic image of a fundus of the subject's eye, and an image of the fundus of the subject's eye, the tomographic image being formed based on combined light obtained by combining return light from the subject's eye to be inspected irradiated with measuring light and reference light which is reflected by a reference mirror, the method comprising:

simultaneously displaying the image of the anterior eye portion, the tomographic image, the image of the fundus, and a pointer for indicating an arbitrary position on a display unit;

detecting a position of the pointer on the display unit;

in response to receiving an instruction indicating a rotation of a wheel of the mouse, adjusting a physical working distance between the ophthalmic apparatus and the subject's eye, in a case that it is detected that the pointer is positioned within the captured image of the anterior eye portion;

in response to receiving the instruction indicating the rotation of the wheel of the mouse, adjusting a physical position of a lens within the ophthalmic apparatus relative to other optical components of the ophthalmic apparatus, wherein the adjustment of the physical position of the lens is for focusing of the image of a fundus of the subject's eye, in a case that it is detected that the pointer is positioned within the captured image of the fundus of the subject's eye; and in response to receiving the instruction indicating the rotation of the wheel of the mouse, adjusting a physical position of the reference mirror within the ophthalmic apparatus relative to other optical components of the ophthalmic apparatus, wherein the adjustment of the physical position of the reference mirror is for adjusting a coherence gate, in a case that it is detected that the pointer is positioned within the captured tomographic image of the subject's eye, and wherein the mouse is operable by the user to control a position of the pointer on the display unit.

* * * * *